(12) United States Patent
Metz et al.

(10) Patent No.: US 6,262,298 B1
(45) Date of Patent: Jul. 17, 2001

(54) PROCESS FOR THE C-ALKYLATION OF MALONIC ESTERS USING PHASE-TRANSFER AGENTS

(75) Inventors: Josef Metz, Marl; Clemens Osterholt, Dorsten, both of (DE)

(73) Assignee: Huels Aktiengesellschaft, Marl (DE)

( * ) Notice: Subject to any disclaimer, the term of this patent is extended or adjusted under 35 U.S.C. 154(b) by 0 days.

(21) Appl. No.: 09/198,581

(22) Filed: Nov. 24, 1998

(30) Foreign Application Priority Data

Nov. 24, 1997 (DE) .............................................. 197 52 041

(51) Int. Cl.⁷ .............................. C07C 67/30; C07C 69/74
(52) U.S. Cl. .......................... 560/203; 560/124; 560/127
(58) Field of Search .................................... 560/124, 127, 560/203

(56) References Cited

PUBLICATIONS

E. V. Dehmlow et al.; Z. Naturforsch.; vol. 43b; 918, (esp. examples on p. 919) 1988.*

* cited by examiner

*Primary Examiner*—Gary Geist
*Assistant Examiner*—Robert W. Deemie
(74) *Attorney, Agent, or Firm*—Oblon, Spivak, McClelland, Maier & Neustadt, P.C.

(57) ABSTRACT

The invention relates to a process for the C-alkylation of dialkyl malonates, in which a dialkyl malonate is reacted with an alkyl halide in the presence of potassium carbonate as a hydrogen halide acceptor in an inert solvent, and a phase-transfer catalyst is not added until from 50 to 80% of the dialkyl malonate has reacted. The phase-transfer catalyst may be, for example, a tetraalkylammonium salt or a tetraalkylammonium hydroxide, a tetraalkylphosphonium salt or a tetraalkylphosphonium hydroxide or a crown ether.

12 Claims, No Drawings

PROCESS FOR THE C-ALKYLATION OF MALONIC ESTERS USING PHASE-TRANSFER AGENTS

BACKGROUND OF THE INVENTION

1. Field of the Invention

The invention relates to a process for the C-monoalkylation or C-dialkylation of a dialkyl malonate with an alkyl halide or an alkylene dihalide having vicinal halogen atoms and potassium carbonate (potash) as the hydrogen halide acceptor.

2. Description of Related Art

DE 43 26 917 describes a process for the preparation of cyclopropane-1,1-dicarboxylic esters from dialkyl malonates and alkylene dihalides having vicinal halogen atoms (referred to below as alkylene dihalides for short) with potassium carbonate as a hydrogen halide acceptor and dimethylformamide or dimethylacetamide as a solvent. In the process, a) alkylene dichlorides are employed, b) potassium carbonate having fine particle fractions of 85% or more smaller than 0.1 mm and 70% or more smaller than 0.05 mm is used, c) the water of reaction is distilled off azeotropically during the reaction, d) the reaction temperature is brought to 90 to 160° C. and e) the molar ratio of dialkyl malonate to alkylene dichloride to potassium carbonate is chosen as 1:(2.5–3.5):(1.0–1.4).

This process constitutes a significant improvement over previously known procedures. Thus, even the cheaply available alkylene dichlorides give yields of more than 80% of theory, which could not be achieved according to D.A. White, Synthetic Communications, 1977, page 599, even with the corresponding alkylene dibromides. Instead of potassium bromide which is difficult to dispose of, potassium chloride, which can be used for the electrolytic preparation of potassium hydroxide, is obtained. The space-time yields for reaction times of from 5 to 6 hours are considerably better than in the process of D.A. White, loc. cit., which requires 22 hours, and in the procedure according to J. Heiszman et al., Synthesis Communications 1987, page 738, in which alkylene dichlorides are employed with benzene as a solvent, a phase-transfer catalyst is used and the reaction time is 20 hours.

There is a need for a process for C-alkylating or dialkyl malonate where the process provides an enhanced conversion of dialkyl malonate relative to conventional processes.

SUMMARY OF THE INVENTION

Accordingly, one object of the present convention is to provide a novel process for C-alkylating dialkly malonates in which the conversation of dialkyl malonate is improved relative to conventional processes. In particular, it has now been found that dialkyl malonates can be advantageously C-alkylated if a dialkyl malonate is reacted with an alkyl halide or an alkylene dihalide in the presence of potassium carbonate in an inert solvent and a phase-transfer catalyst is not added until from about 50% to about 80% of the dialkyl malonate has reacted.

DETAILED DESCRIPTION OF THE INVENTION

In the process of the present invention, if an alkyl halide and an unsubstituted dialkyl malonate are used, the monosubstituted or the disubstituted derivative is obtained, depending on the molar ratio of dialkyl malonate to alkyl halide to potassium carbonate. For the preparation of C-monosubstituted dialkyl malonates, the substances are advantageously used in a molar ratio of 1:(1.5–3.0):(0.4–0.6), in particular of 1:(2.0–2.5):(0.45–0.5) takes place according to the equation

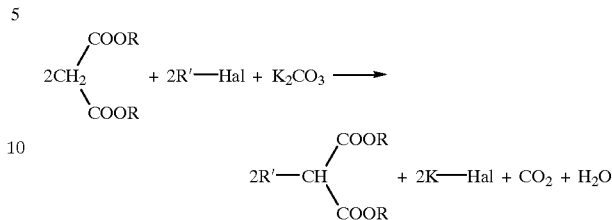

Here, R and R' denotes an alkyl radical. Hal denotes a halide. For the preparation of dialkylated derivatives, a molar ratio of 1:(2.5–4.5):(1.0–1.5), in particular of 1:(2.5–3.0):(1.1–1.3), is advantageously chosen. A special case of the dialkylated derivatives comprises the cyclopropane compounds which are obtained if an alkylene dihalide or 1,2-alkylene dihalide is used as a starting material:

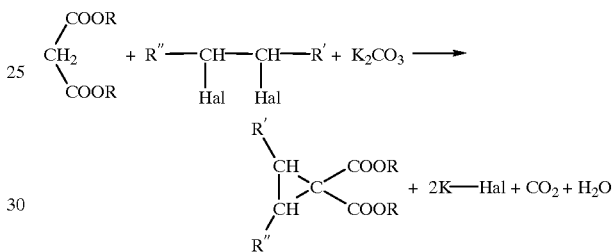

Here, R, R' and R" independently each denote an alkyl radical or hydrogen. In this case, a molar ratio of 1:(2.5–3.5):(1.0–1.4), advantageously of 1:(2.5–3.0):(1.0–1.4), is advisable.

C-Monoalkylated dialkyl malonates can be converted by the process according to the invention into dialkyl-substituted derivatives. Disubstituted dialkyl malonates having different alkyl substituents can be prepared in this manner.

Surprisingly, in the process according to the invention, the reaction times can be shortened considerably—to 3 hours in the case of the stated process for the preparation of cyclopropane-1,1-dicarboxylic esters—and the space-time yields correspondingly increased.

Many of the dialkyl malonates used as starting materials are available in commercial quantities. Dialkyl malonates having $C_{1-4}$-alkyl radicals, such as dimethyl malonate (DMM) and diethyl malonate (DEM), which are preferred, and diisopropyl malonate and di-n-butyl malonate, may be mentioned as examples of suitable dialkyl malonates.

Preferred alkyl halides, including, for example, alkylene dihalides or 1,2-alkylene dihalides, are the chlorides. Suitable alkyl chlorides and alkylene dichlorides have in general up to 12, in particular up to 6, carbon atoms. For example, methyl chloride (can be reacted only under superatmospheric pressure), ethyl chloride, isopropyl chloride, allyl chloride, isoamyl chloride, 2-chlorohexane, 1-chlorooctane, 1,2-dichloroethane (i.e., ethylene dichloride, EDC), 1,2-dichloropropane, 2,3-dichlorobutane and 1,2-dichlorocyclohexane may be mentioned specifically.

The potassium carbonate used is the usual product, which is free of water of crystallization and which has been brought to a fine particle size by milling, for example in ball mills or pinned-disk mills. A potassium carbonate having fine particle fractions of 85% or more smaller than 0.1 mm and 70% or more smaller than 0.05 mm is particularly suitable.

Suitable inert solvents which are expediently concomitantly used are in particular dimethylformamide (DMF), dimethylacetamide (DMA) and N-methyl-2-pyrrolidone (NMP). dimethylformamide (DMF), dimethylacetamide (DMA), and N-methyl-2-pyrrolidone (NMP). They are expediently used in 3 to 4 times the amount by weight, based on the weight of the dialkyl malonate.

The water of reaction is expediently removed from the reaction mixture with the aid of an entraining agent. If dialkylated malonic esters are prepared, excess alkyl halide or alkylene dihalide can be used as entraining agent. This is also possible in the conversion of alkyl halides to monoalkylated derivatives, by using, for example, stoichiometric amounts of alkyl halide and recycling the alkyl halide distilled off with the water to the reaction after condensation and phase separation. Alternatively, it is also possible to add one of the conventional inert entraining agents, e.g. toluene.

An important feature of the process according to the invention is that the reaction can be carried out to a dialkyl malonate conversion of from 50 to 80% and thereafter a phase-transfer catalyst is added and the reaction is completed.

The phase-transfer catalyst facilitates the interaction of the reactants present in the liquid phase with the solid potassium carbonate, as is evident from the increased evolution of carbon dioxide, which is triggered by the addition of the phase-transfer catalyst. Suitable phase transfer catalysts are, for example, quaternary ammonium salts, such as tetraalkylammonium salts, advantageously having $C_1$- to $C_8$-alkyl radicals and in particular having $C_1$- to $C_4$-alkyl radicals, and the corresponding ammonium hydroxides, such as a tetraalkylammonium hydroxide such as tetra-n-butylammonium hydroxide. The salts may be, for example, halides, hydrogen sulfates or sulfates. For example, tetrabutylammonium bromide (TBAB), tetra-n-butylammonium bromide, tetrabutylammonium hydrogen sulfate, tetra-n-butylammonium hydrogen sulfate, tetraoctylammonium bromide, benzyltriethylammonium chloride and methyltrioctylammonium chloride may be mentioned as typical members of these classes of substance. The corresponding phosphonium compounds, such as a tetraalkylphosphonium salt, a tetraalkylphosphonium hydroxide, tetra-n-butylphosphonium hydroxide and tetra-n-butylphosphonium bromide, are also suitable. Other phase-transfer catalysts which may be used in the present invention are crown ethers, in particular 18-crown-6. Phase transfer catalysts are expediently used in from 0.003 to 0.01 times the amount by weight, based on the weight of the dialkyl malonate. With these small amounts, disposal presents no particular problems, and no significant amounts of amines are obtained even at relatively high temperatures during the, working up, at which decomposition must occur.

For carrying out the process according to the invention, the organic reactants, the potassium carbonate and the solvent and optionally an inert entraining agent may be taken in a reaction vessel and the mixture heated to the reaction temperature of from about 90° C. to about 160° C., expediently with stirring. The azeotropic mixture distilling off is condensed, the phases are allowed to separate, the phase comprising the water of reaction is removed and the organic phase is recycled to the reaction vessel. The progress of the reaction is monitored by means of exit gas measurements and GC analyses of the reaction mixture.

As soon as the reaction declines and from 50 to 80%, advantageously from 60 to 70%, of the dialkyl malonate has reacted, the phase-transfer catalyst is added, expediently gradually in the course of from 15 to 45 minutes, after which the reaction is once again initiated, this being detectable from the vigorous evolution of carbon dioxide. The phase-transfer catalyst can be added as an aqueous solution. After a total of from 3 to 17 hours, the reaction is virtually complete. In this way, a dialkyl malonate conversion of >98% can be achieved, for example in the preparation of dimethyl cyclopropane-1,1-dicarboxylate. If the phase-transfer catalyst is used as early as the beginning of the reaction, a conversion of only 93% is achieved under otherwise identical conditions and the excess potassium carbonate is consumed predominantly for the intramolecular dehydrochlorination of the halogen compound with the formation of olefinically unsaturated compounds.

The products of the process are known substances and valuable intermediates for further syntheses, for example in the pharmaceutical and crop protection sectors.

Having generally discussed this invention, a further understanding can be obtained by reference to certain specific examples which are provided herein for purposes of illustration only and are not intended to be limiting unless otherwise specified.

EXAMPLES

Example 1

Dimethyl cyclopropane-1,1-dicarboxylate 2.1 mol of DMM, 6.6 mol of EDC, 2.4 mol of potash having fractions of 87% by weight with particle sizes of <0.1 mm and fractions of 78% by weight with particle sizes of <0.05 mm and 6.5 mol of DMF are taken in a reaction vessel having a stirrer and distillation attachment with condenser and phase separation vessel. The mixture is heated to 110° C. with stirring, water of reaction distilling off azeotropically with EDC. The water of reaction is taken off as the upper phase, and the EDC, the lower phase, is recycled to the reaction.

After 1.5 h, 65% of the DMM has been converted. 0.008 mol of TBAB as a 50% strength by weight aqueous solution is added in the course of 30 min. The evolution of carbon dioxide increases again. After a further hour, i.e. after 3 h from the beginning of the reaction, a DMM conversion of about 98% is reached. The reaction is then complete; the reaction of the remaining DMM takes place in the subsequent working-up stage.

Excess EDC is distilled off from the reaction mixture, initially at a temperature of from 110 to 120° C., the DMM conversion increasing to >99%. Volatile fractions of high boilers and salt are then separated off using a rotary evaporator (160° C., 1 mbar). The distillate, predominantly DMF and the desired product dimethyl cyclopropane-1,1-dicarboxylate, is subjected to fractional distillation. The desired product is obtained in a purity of 99.3% (GC analysis) and with a yield of about 83% of theory, based on DMM used.

The exit gas escaping from the reaction (predominantly $CO_2$ and a small amount of $H_2O$, vinyl chloride and EDC) is fed to an incineration unit for chlorinated hydrocarbons. The valuable substances EDC and DMF obtained in the working up of the reaction batch by distillation can be used for a further batch.

Comparative Example 1

The procedure is as in Example 1, except that the phase-transfer catalyst is used as early as the beginning. Under otherwise identical conditions, more potash is consumed for the formation of vinyl chloride. After 3 hours, scarcely any potash was present but only 93% of the DMM had reacted.

Example 2

Diethyl n-butylmalonate 6.0 mol of DMF, 2.5 mol of n-butyl chloride (n-BuCl), 0.95 mol of potassium carbonate according to Example 1 and 2 mol of DEM are taken. The mixture is heated to 110–120° C. with stirring, the water of reaction distilling off azeotropically with n-BuCl. The water of reaction is removed as the lower phase after condensation of the azeotropic mixture, and n-BuCl, the upper phase, is recycled. In order to maintain a sufficiently high distillation performance, a further 2 mol of n-BuCl are metered in during the reaction. After a reaction time of 2 hours, 0.008 mol of TBAB, as a 50% strength by weight aqueous solution, is metered in within 30 min.

After a total reaction time, of 6 h, a DEM conversion of 92%, determined by GC analysis, is reached. When the remaining n-BuCl is separated off, the conversion increases to 93.5%. The further working up is carried out analogously to Example 1. The desired product is obtained in a purity of >99% (GC analysis) and the yield is 85% of theory, based on the DEM conversion. The valuable substances n-BuCl, DEM and DMF obtained in the working up of the reaction batch by distillation can be used for a further batch.

Example 3

Diethyl n-propylmalonate 6 mol of NMP, 1.2 mol of n-propyl chloride (n-PrCl), 2.4 mol of potassium carbonate according to Example 1 and 2 mol of DEM are taken. The reaction is carried out analogously to Example 2 over a total reaction time of 17 hours. After 2 h and 7 h, in each case 0.008 mol of TBAB is metered in as a 50% by weight aqueous solution. 4.8 mol of n-BuCl are metered in within the total reaction time.

The desired product is obtained in a purity of >99% (GC analysis) and the yield is about 78% of theory, based on the DEM used. The valuable substances n-PrCl, diethyl mono-n-propylmalonate and NMP obtained in the working up of the reaction batch by distillation can be used for a further batch.

Example 4

Diethyl ethylmalonate 6 mol of DMF, 0.95 mol of potassium carbonate according to Example 1 and 2 mol of DEM are taken. The reaction is carried out at 110–120° C. analogously to Example 2 over a total reaction time of 6 h. During this time, 5 mol of 1-chloroethane are passed in. The condenser is adjusted to about 1° C. using a cryostat, and the upper phase of the condensed azeotropic mixture consists of 1-chloroethane and is recycled to the reaction. After a reaction time of 2.5 h, the phase-transfer catalyst (0.008 mol of TBAB as a 50% strength by weight aqueous solution) is added.

The DEM conversion after 6 h is about 98% of theory. After the working up of the reaction mixture by distillation, the desired product is obtained in a purity of >99% (GC analysis). The yield is about 86% of theory based on the DEM conversion.

Obviously, numerous modifications and variations of the present invention are possible in light of the above teachings. It is therefore to be understood that within the scope of the appended claims, the invention may be practiced otherwise than as specifically discussed herein.

What is claimed is:

1. A process for the C-alkylation of a dialkyl malonate, comprising
   reacting a mixture of a dialkyl malonate, an alkyl halide, potassium carbonate, and an inert solvent; and
   adding a phase-transfer catalyst to the mixture after about 50% of the dialkyl malonate has reacted.

2. The process as claimed in claim 1, wherein the alkyl halide is an alkylene dihalide.

3. The process as claimed in claim 2, wherein the alkylene dihalide is a 1,2-alkylene dihalide.

4. The process as claimed in claim 1, wherein the phase-transfer catalyst is added to the mixture when between about 50% and about 80% of the dialkyl malonate has reacted.

5. The process as claimed in claim 1, wherein the phase-transfer catalyst is added to the mixture when between about 60% and about 70% of the dialkyl malonate has reacted.

6. The process as claimed in claim 1, wherein the dialkyl malonate is dimethyl malonate or diethyl malonate.

7. The process as claimed in claim 1, wherein potassium carbonate having fine particle fractions of 85% by weight or more smaller than 0.1 mm and 70% by weight or more smaller than 0.05 mm is used.

8. The process as claimed in claim 1, wherein the alkyl halide is an alkyl chloride.

9. The process as claimed in claim 1, wherein the phase transfer catalyst is a tetraalkylammonium salt or a tetraalkylammonium hydroxide, a tetraalkylphosphonium salt or a tetraalkylphosphonium hydroxide or a crown ether.

10. The process as claimed in claim 9, wherein the phase-transfer catalyst is tetra-n-butylammonium bromide, tetra-n-butylammonium hydrogen sulfate, tetra-n-butylphosphonium bromide or 18-crown-6.

11. The process as claimed in claim 1, wherein the inert solvent used is dimethylformamide, dimethylacetamide or N-methyl-2-pyrrolidone.

12. The process as claimed in claim 1, wherein the reaction is carried out at temperatures of from about 90° C. to about 160° C. with removal of water of reaction by azeotropic distillation.

* * * * *